US010813606B2

(12) United States Patent
Seo et al.

(10) Patent No.: US 10,813,606 B2
(45) Date of Patent: Oct. 27, 2020

(54) MULTI-AXIALLY VARIABLE DETECTION MODULE OF PET APPARATUS

(71) Applicants: GACHON UNIVERSITY OF INDUSTRY-ACADEMIC COOPERATION FOUNDATION, Seongnam-si, Gyeonggi-do (KR); GIL MEDICAL CENTER, Incheon (KR)

(72) Inventors: Seong-Ho Seo, Seoul (KR); Sang-Yoon Lee, Incheon (KR); Jun-Young Chung, Incheon (KR); Ji-Hye Lee, Incheon (KR)

(73) Assignees: Gachon University of Industry-Academic Cooperation Foundation, Seongnam-si, Gyeonggi-do (KR); GIL Medical Center, Incheon (KR)

( * ) Notice: Subject to any disclaimer, the term of this patent is extended or adjusted under 35 U.S.C. 154(b) by 0 days.

(21) Appl. No.: 16/304,641

(22) PCT Filed: Oct. 31, 2017

(86) PCT No.: PCT/KR2017/012192
§ 371 (c)(1),
(2) Date: Mar. 26, 2019

(87) PCT Pub. No.: WO2018/080289
PCT Pub. Date: May 3, 2018

(65) Prior Publication Data
US 2019/0261934 A1 Aug. 29, 2019

(30) Foreign Application Priority Data
Oct. 31, 2016 (KR) .................. 10-2016-0143477

(51) Int. Cl.
A61B 6/00 (2006.01)
A61B 6/03 (2006.01)
G01T 1/29 (2006.01)

(52) U.S. Cl.
CPC .............. A61B 6/4208 (2013.01); A61B 6/00 (2013.01); A61B 6/03 (2013.01); A61B 6/037 (2013.01); A61B 6/4275 (2013.01); G01T 1/2985 (2013.01)

(58) Field of Classification Search
CPC ................................ A61B 6/4208; A61B 6/00
See application file for complete search history.

(56) References Cited

U.S. PATENT DOCUMENTS

2002/0148970 A1 10/2002 Wong et al.
2011/0026685 A1* 2/2011 Zilberstein ............. A61B 6/037
378/197
(Continued)

FOREIGN PATENT DOCUMENTS

JP 2004-533607 A 11/2004
JP 2008-175775 A 7/2008
(Continued)

OTHER PUBLICATIONS

Jorge Uribe et al., "Gantry Design With Accurate Crystal Positioning for a High-Resolution Transformable PET Camera", IEEE Transactions on Nuclear Science, Feb. 2005, pp. 119-124, vol. 52, No. 1.
(Continued)

Primary Examiner — Hugh Maupin
(74) Attorney, Agent, or Firm — Rabin & Berdo, P.C.

(57) ABSTRACT

Disclosed is a multi-axially variable detection module of a PET apparatus, the detection module including: a gantry having a through-hole extending from a side to an opposite side of the gantry; a detection module in which a plurality of detectors for detecting gamma rays emitted from a subject are arranged annularly along an inner circumference of the gantry; and a driving means for moving the plurality of detectors constituting the detection module in a radial direction of the detection module, wherein each of the plurality of detectors is rotatable in a longitudinal direction of the detection module to vary a length thereof in the longitudinal direction, and each of the plurality of detectors include multiple detector elements which are engaged with each other in a hinged manner in a transverse direction (circumferential direction) of the detection module to form a flat or an arc shape.

11 Claims, 10 Drawing Sheets

(56) References Cited

U.S. PATENT DOCUMENTS

2014/0367577 A1* 12/2014 Badawi ............... A61B 6/4411
 250/366
2015/0119704 A1  4/2015 Roth et al.

FOREIGN PATENT DOCUMENTS

| KR | 10-2010-0122596 A | 11/2010 |
| KR | 10-1123951 B1 | 4/2012 |
| KR | 10-2015-0062642 A | 6/2015 |
| KR | 10-1662015 B1 | 10/2016 |
| WO | WO 02/079802 A2 | 10/2002 |

OTHER PUBLICATIONS

International Search Report dated Oct. 31, 2017.

* cited by examiner

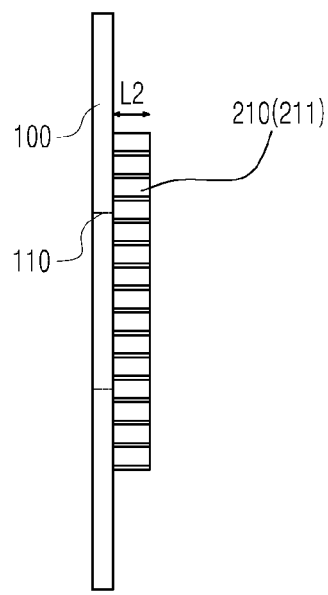 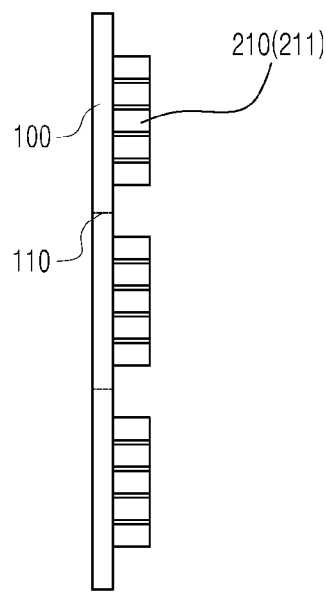 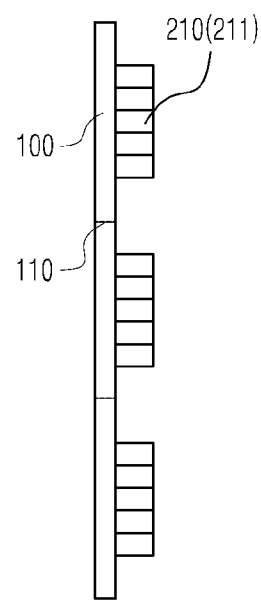
FIG. 8A          FIG. 8B          FIG. 8C
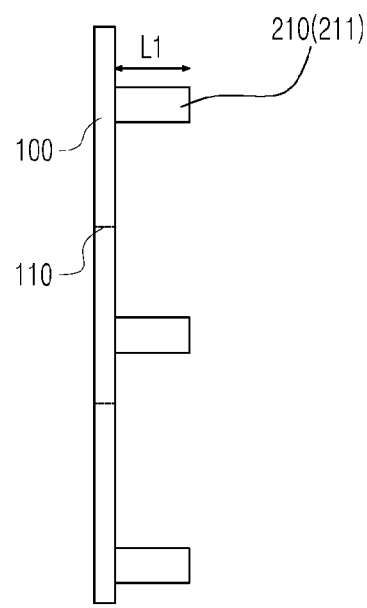 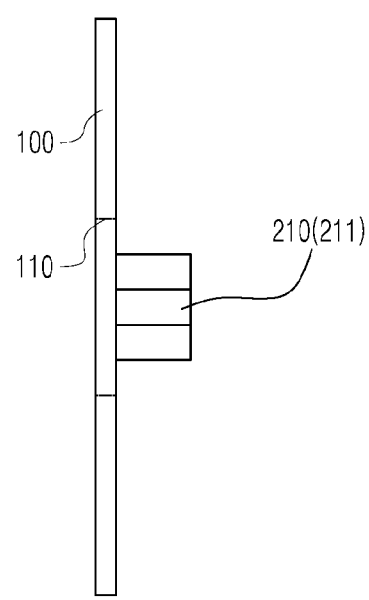
FIG. 8D          FIG. 8E

MULTI-AXIALLY VARIABLE DETECTION MODULE OF PET APPARATUS

TECHNICAL FIELD

The present invention relates to a variable detection module of a positron emission tomography (PET) apparatus. More particularly, the present invention relates to a variable detection module of a PET apparatus, the detection module varying an arrangement of the detection module in transverse and longitudinal directions according to a size of an subject and a purpose of imaging and being extended in length in the longitudinal direction by rotation of detectors while a shape thereof is maintained regardless of a variation in diameter of the detection module.

BACKGROUND ART

Positron emission tomography (PET) is one of the nuclear medicine functional imaging techniques that provides imaging of physiological and biochemical processes of the human body in three dimensions using radiopharmaceuticals that emit positrons.

These days, PET is widely used in diagnosis of various cancers and is known as a useful test for differential diagnosis, staging, evaluation of recurrence, and evaluation of treatment effect, and the like, of cancer.

In addition, PET is used to obtain receptor images or metabolic images for diagnosis of cardiac diseases, cerebral diseases, and brain function assessment.

A positron refers to an antiparticle that has physical properties similar to an electron with negative (−) charge, but has positive (+) charge. Positrons are emitted from radioisotopes such as C-11, N-13, O-15, F-18, etc., as one type of radiation. Since such elements are major constitutional elements of biomaterial, a radiopharmaceutical thereof can be utilized as a tracer for tracking a specific physiological, biochemical or functional change.

For example, F-18-FDG, a radioactive medicine most frequently used, is a glucose-like material. A large amount of F-18-FDG gathers in a specific area of glucose hypermetabolism such as in cancer when injected in a body.

A positron emitted from radioisotopes consumes all of its own kinetic energy in a short time after emission. Then, the positron undergoes annihilation by colliding with neighboring electrons. At this point, two annihilation radiations (511 keV annihilation photons; e.g., gamma-ray) are emitted at an angle of 180°.

A cylindrical PET scanner (hereinafter, referred to as a PET apparatus) is a device capable of detecting two annihilation radiations emitted simultaneously. By reconstructing images using radiation detected thereby, it is possible to display by way of a three-dimensional tomographic image used for determining how much and where radiopharmaceuticals are concentrated in the body.

A part of the body displaying an abnormally strong signal due to accumulation of radiopharmaceuticals in PET images can subsequently be diagnosed as a cancer.

Sensitivity and resolution are important elements in assessing performance of a PET apparatus.

A PET apparatus mainly used for human beings these days is categorized according to a subject to be imaged, for example: into a PET apparatus only for brains (not illustrated) and a PET apparatus 1 for the whole body as illustrated in FIG. 1.

The PET apparatus 1 includes a detection module 10 detecting radiation emitted from a human body. The detection module 10 is provided with multiple detectors 11 arranged in an annular shape as illustrated in FIG. 2.

The detectors 11 are constituted of a scintillation crystal and a photomultiplier tube (PMT), and the detectors 11 are disclosed in Korean Patent No. 10-1123951.

The conventional PET apparatus 1 including the annular detection module 10 provided with the multiple detectors 11 is provided for imaging a whole body and a brain of a human being. Assuming that the apparatus is provided a predetermined length along the longitudinal axis (V), a diameter D0 of the detection module 10 is fixed to be suitable for a whole body. Thus, when imaging a brain, there is a problem in that the accuracy of the measurement result for a brain is lower than that of a whole body.

Since a diameter of a brain is smaller than that of a whole body, a distance between the brain and the detector 11 is far, leading to low sensitivity and resolution. There is a problem in that the accuracy of the brain imaging is lowered compared with the whole body imaging even though the same PET apparatus 1 is used.

Sensitivity and resolution, which are important performance indicators of the PET apparatus, are affected by a geometry of the PET apparatus in accordance with an arrangement of the detection module 10. Therefore, in order to obtain the best image quality, it is ideal to use equipment that corresponds to the cross-sectional diameter of the subject from the structural aspect.

In other words, when imaging a small subject such as a brain, it is appropriate to use a brain-dedicated PET apparatus. For a larger subject, it is appropriate to use a whole body-dedicated PET apparatus.

However, it is economically burdensome for users to have PET apparatuses 1 having different diameters of the detection module 10 in accordance with purposes of PET imaging.

In order to solve the problem, a multi-purpose variable PET apparatus (Korean Patent Application No. 10-2016-50533) is disclosed, which can be adapted to subjects having various sizes by varying a diameter of a detection module 10 in accordance with a size of a subject.

However, in the conventional PET apparatus, the detector moves only in a radial direction to vary only a diameter on a transverse section corresponding to a size of a subject, which means that the efficiency in the longitudinal direction is not considered.

Therefore, in the case where the detection module 10 having a diameter for a whole body varies in diameter to correspond to a subject smaller than the whole body, a detection module capable of extension in the longitudinal direction is required.

Accordingly, as illustrated in FIG. 3, an apparatus for implementing a variable length in the longitudinal direction through the rotation of each detector 11 constituting the detection module 10 has been proposed, but the apparatus has the following problems.

In order to secure a sufficient length in the longitudinal direction, a size of the detection module 10 in the transverse section is required to be increased. As a result, a shape of the detection module 10 is distant from the ideal annular shape, and the structural sensitivity on the transverse section is deteriorated.

That is, when long sides of the detectors 11 constituting the detection module 10 are provided to be long, there is an advantage in that the length in the longitudinal direction can be secured through the rotation of the detector 11. However, when the long sides thereof constitute an arc of the detection module 10, it is difficult to optimize the sensitivity because the shape of the detection module 10 is difficult to define annular shape due to a flat shape of the excessive length of the long sides.

DOCUMENTS OF RELATED ART

Patent Document

1. Korean Patent Application Publication No. 10-2016-50533

Non-Patent Document

1. Gantry Design With Accurate Crystal Positioning for a High-Resolution Transformable PET Camera
2. IEEE TRANSACTIONS ON NUCLEAR SCIENCE, VOL. 52, NO. 1, FEBRUARY 2005

DISCLOSURE

Technical Problem

Accordingly, the present invention has been made keeping in mind the above problems occurring in the related art, and the present invention is intended to provide a multi-axially variable detection module of a PET apparatus, the detection module being configured such that each detector constituting the detection module includes multiple detector elements engaged with each other in a hinged manner to form an arc shape such that an arrangement of the detection module having a substantially annular shape is maintained even though the detection module is variable in diameter and thus having advantages such as: varying a transverse sectional structure in accordance with a size of a subject; varying in length in a longitudinal direction by rotation of detectors; and maintaining the sensitivity regardless of a variation in diameter of the detection module.

Technical Solution

In order to accomplish the above objective, the present invention provides a multi-axially variable detection module of a PET apparatus, the detection module including: a gantry having a through-hole extending from a side to an opposite side of the gantry; a detection module in which a plurality of detectors for detecting gamma rays emitted from a subject are arranged annularly along an inner circumference of the gantry; and a driving means for moving the plurality of detectors constituting the detection module in a radial direction of the detection module, wherein each of the plurality of detectors is rotatable in a longitudinal direction of the detection module to vary a length thereof in the longitudinal direction, and each of the plurality of detectors includes multiple detector elements which are engaged with each other in a hinged manner in a transverse direction (circumferential direction) of the detection module to form a flat or an arc shape.

Two or more detectors may be engaged with each other in a hinged manner to constitute the detector module.

The driving means may be configured to generate power for rotating the detector, and to push or pull end sides of the multiple detector elements to arrange the detectors in a flat or an arc shape.

The driving means may include: a first drive unit generating linear driving force and rotational power; a drive shaft linearly moved by the power of the first drive unit and rotated about the first drive unit; and a second drive unit branched from the drive shaft into two ends, corresponding to the outermost detector elements constituting the detector, and generating a translational force.

The multiple detector elements may be configured in a grid arrangement in the longitudinal and transverse directions of the detection module, and the detector elements configured in a grid arrangement in the longitudinal direction may be engaged with each other in a hinged manner.

Advantageous Effects

A multi-axially variable detection module of a PET apparatus according to the present invention has the following effects.

First, detectors constituting a detection module are configured such that a length thereof in a transverse direction is longer than a length thereof in a longitudinal direction to extend the length in the longitudinal direction through rotation of the detectors, and each detector is configured with multiple detector elements engaged with each other in a hinged manner such that the detector elements can be rotated about hinges and arranged in an arc shape, whereby a sensitivity loss that may occur due to the detectors arranged in a flat shape in the transverse direction can be prevented.

In other words, a shape of the detection module is required to be an ideal circular shape (annular shape) for optimal sensitivity, and if the length of the detector in the transverse direction is longer than that in the longitudinal direction, the curve of the detection module is difficult to approach the circular shape. Thus, by artificially arranging the detectors to be curved through the rotation of the hinge shaft of the detector elements, it is possible to keep the shape of the detection module circular by arranging the detectors in a curve through rotation of the detection elements about the hinges.

Accordingly, the shape of the detection module can be maintained in a circular shape regardless of a variation in diameter of the detection module, whereby the sensitivity of PET imaging is not deteriorated.

Second, in order to extend transverse lengths of the detectors, which correspond to the longitudinal length of the detector module, two or more detectors are combined in a hinged manner such that the transverse lengths of the detectors are extended, leading to extension of the longitudinal length of the detector module.

Third, the detection module can be extended in the longitudinal direction in a process of reducing the diameter of the detection module to image a subject having a small size.

Accordingly, a solid angle of the detection module is increased, thereby improving the structural sensitivity.

In other words, a space for radiation emitted from a subject is further secured in the longitudinal direction of the detection module such that radiation leakage can be prevented and the detection efficiency can be maximized.

Particularly, in the three-dimensional image reconstruction, the sensitivity of the PET imaging can be further improved because the number of lines of response (LORs) required in the reconstruction increases due to the detection module extending in the longitudinal direction.

Fourthly, it is possible to provide an optimum environment for imaging a subject regardless of size thereof without providing additional equipment such that the sensitivity in imaging can be optimized.

Particularly, the cost required for additional equipment can be omitted. Thus, in terms of a cost aspect, it is possible to increase the efficiency of equipment operation.

BRIEF DESCRIPTION OF THE DRAWINGS

FIGS. 8a to 8e are side views illustrating a process of varying a diameter of the multi-axially variable detection module of a PET apparatus according to the embodiment of the present invention in the radial direction;

BEST MODE

Terms or words used in the specification and claims are not limited to a meaning that is commonly understood by people or is defined in dictionaries, and should be interpreted as having a meaning that is consistent with meaning in the context of the relevant art.

Hereinafter, a variable detection module of a positron emission tomography (PET) apparatus according to an embodiment of the present invention will be described with reference to FIGS. 4 to 8 attached hereto.

A multi-axially variable detection module of a PET apparatus has a technical feature that a length in the longitudinal direction of the detection module is extended in a process in which a diameter of the detection module is contracted in a radial direction (transverse direction).

Accordingly, the sensitivity of the apparatus detecting radiation is improved structurally due to an increase in a solid angle of the detection module, and the efficiency of use of detectors is increased through the use of all detectors.

Figure 1:
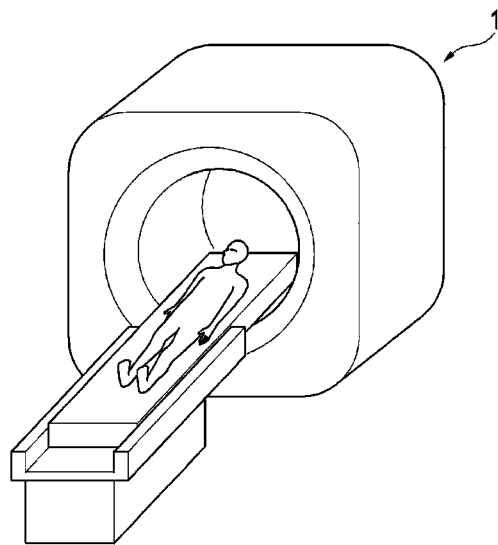
FIG. 1 is a schematic view illustrating a positron emission tomography (PET) apparatus according to the related art.
Figure 2:
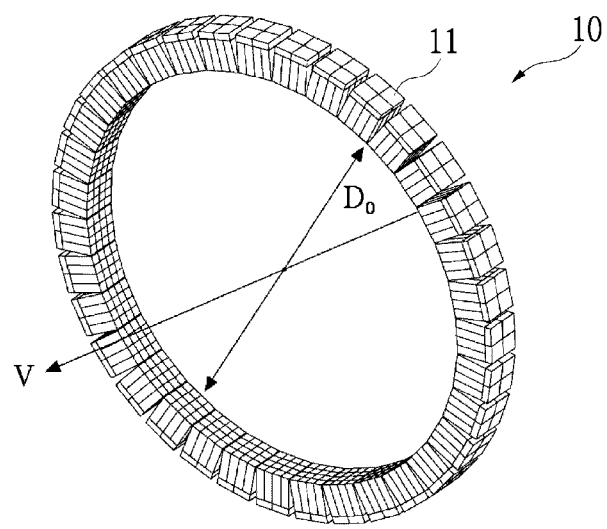
FIG. 2 is a perspective view illustrating an annular detection module constituting a PET apparatus according to the related art.
Figure 3:
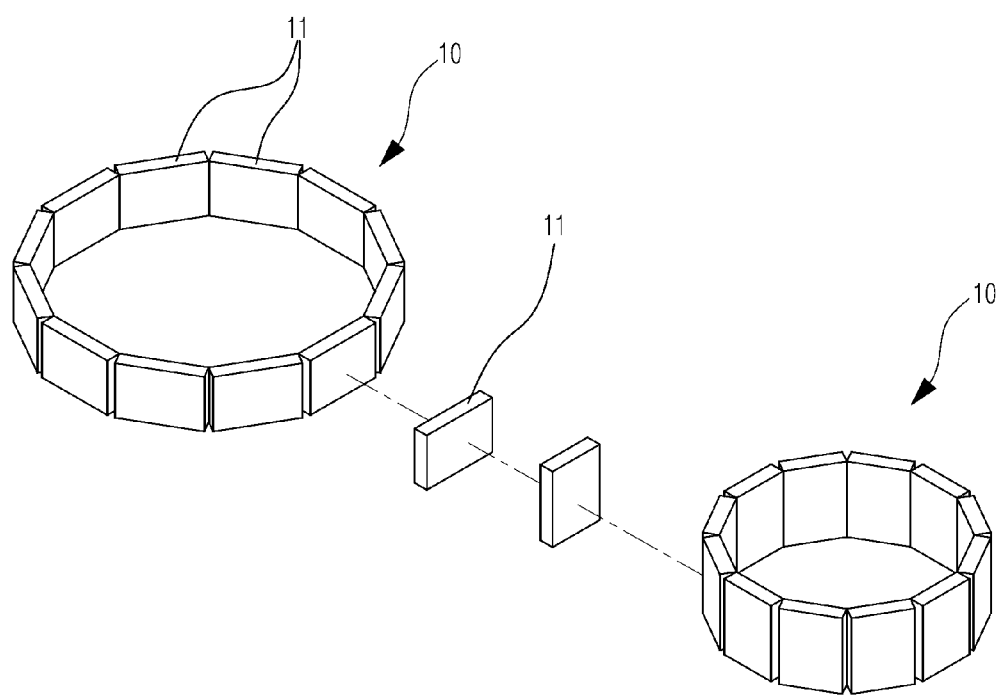
FIG. 3 is a perspective view illustrating a state in which an annular detection module constituting a PET apparatus according to the related art is variable in length in a longitudinal direction of the detection module through rotation of each detector.
Figure 4:
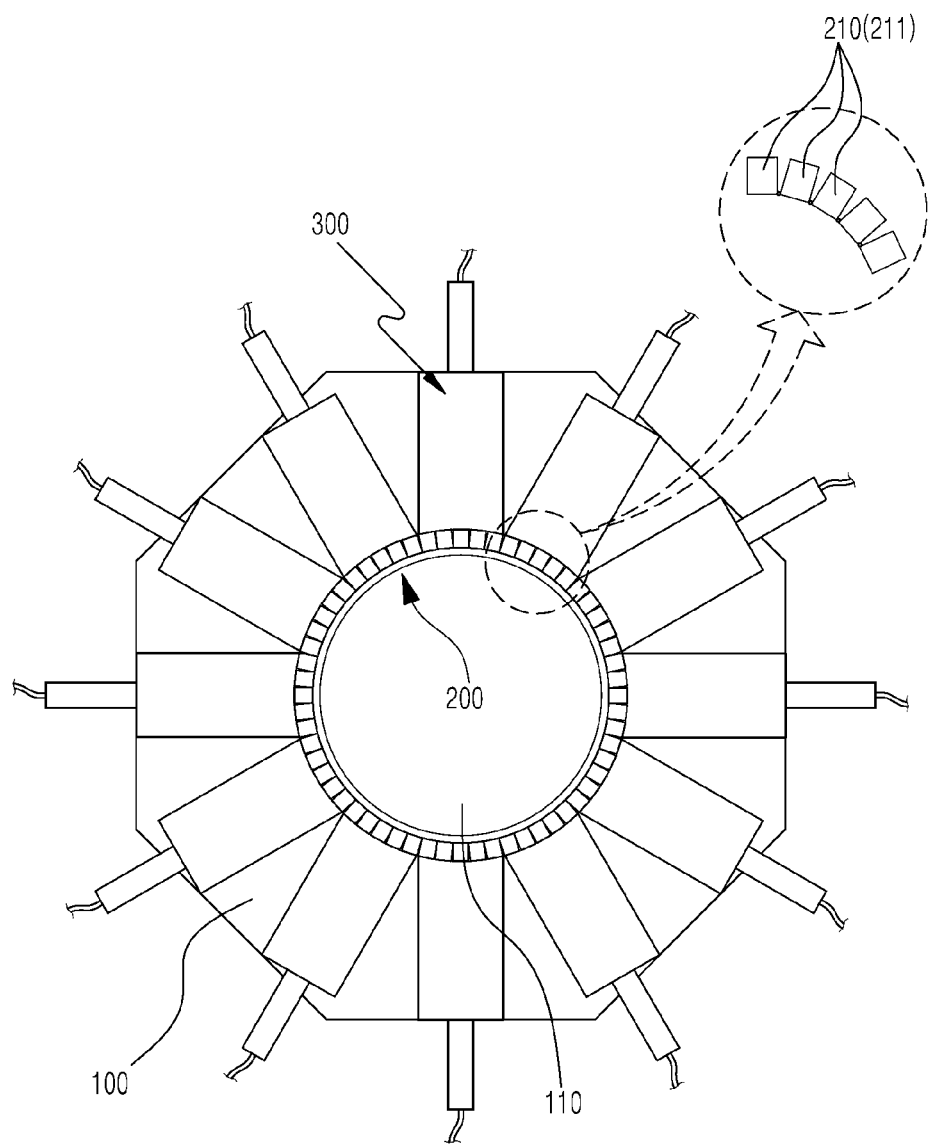
FIG. 4 is a front view illustrating a state in which a multi-axially variable detection module of a PET apparatus according to an embodiment of the present invention is provided on a gantry.

The variable detection module of a PET apparatus includes a gantry 100, a detection module 200, and driving means 300 as illustrated in FIG. 4.

The gantry 100 has a through-hole 110 extending from a side to an opposite side of the gantry 100 to accommodate a subject and is configured in a panel form such the detection module 200 and the driving means are provided thereon.

Here, although a shape of the gantry 100 is not limited, the gantry 100 may have any shape that provides a structure in which the detection module 200 is provided in an annular shape.

The detection module 200 is configured with a plurality of detectors 210. The plurality of detectors 210 are arranged annularly along an inner circumference of the gantry 100.

The detectors 210 are configured with one or more scintillation crystals that convert gamma rays into light and one or more photomultiplier tubes (PMTs) that convert light into an electrical signal.

Here, a solid state light sensor such as an avalanche photodiode and a silicon photomultiplier may be used in place of the photomultiplier.

The detection module 200 array may have a ring-shaped or a polygonal transverse section. In order to obtain a high sensitivity, it is preferable that the detection module 200 array has a substantially circular ring shape.

Each of the detectors 210 constituting the detection module 200 is configured with multiple detector elements 211.

That is, as illustrated in FIG. 4, the multiple detector elements 211 are combined to constitute a long side (in the transverse direction) length of each detector 210.

Here, the multiple detector elements 211 are engaged to each other in the circumferential direction of the detection module in a hinged manner.

Such a configuration is advantageous in that the long side of the detector 210 varies in the longitudinal direction of the detection module through the rotation of the detector 210. However, when the length of the long side of the detector 210 is long, the entire shape of the detection module 200 is configured in an angled polygon shape rather than an annular shape, whereby a sensitivity loss to the radiation detection may occur.

Accordingly, as the detector 210 is configured with the multiple detector elements 211 that can be curved about hinges as described above, the entire shape of the detection module 200 can be maintained in the annular shape even when the length of the long side of the detector 210 is long. Thus, it is possible to prevent loss of sensitivity.

The number of detector elements 211 constituting the detector 210 is not limited, and the number of scintillation crystals and the number of PMTs are not required to be provided equally.

For example, multiple scintillation crystals may be provided per PMT. However, it is preferable that one scintillation crystal is provided for each PMT.

The driving means 300 drive the detectors 210 in the transverse direction (radial direction) and generate power for varying a diameter of the detection module 200.

As illustrated in FIG. 4, the driving means 300 are provided on the gantry 100 and vary the diameter of the detecting module 200 by pushing or pulling each detector 210.

The driving means 300 are provided on a front or back surface of the gantry 100.

Figure 5A:
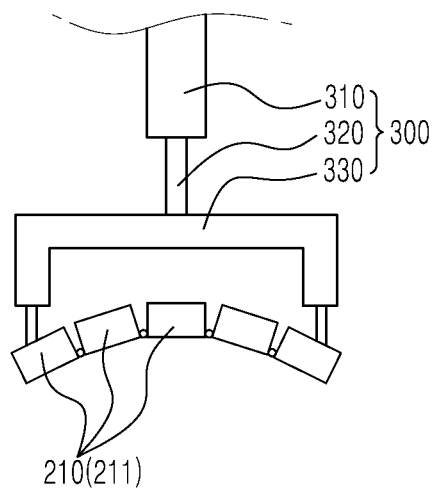
FIG. 5a is a schematic view illustrating a state in which a driving means is provided on a detector constituting the multi-axially variable detection module of a PET apparatus according to the embodiment of the present invention and detector elements are rotated around hinges such that the detector is configured in an arc shape.

In addition, the driving means 300 may be any device capable of generating a linear motion and will be described in more detail with reference to FIGS. 5a to 5c.

The driving means 300 drive the detectors 210 in the longitudinal direction with respect to the through-hole 110 of the gantry 100 and generate power for rotating the detectors 210 and power for converging or distributing the multiple detector elements 211.

It is preferable that each of the driving means 300 includes a first drive unit 310, a drive shaft 320, and a second drive unit 330.

The first drive unit 310 generates linear driving force and rotational driving force, and pushes or pulls the drive shaft 320.

The first drive unit 310 generates power for rotating the drive shaft 320.

The drive shaft 320 is configured to be drawn out from the first drive unit 310 or retracted into the first drive unit 310 while rotating around the first drive unit 310.

The second drive unit 330 is branched from the drive shaft 320 into two ends and provided corresponding to the outermost sides of the multiple detector elements 211.

The second drive unit 330 generates power for pushing or pulling out the outermost detector elements 211.

Figure 5B:
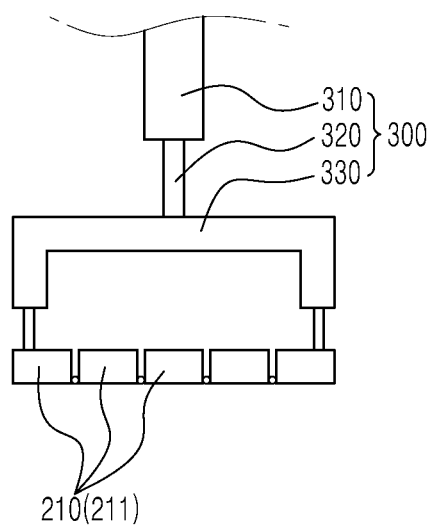
FIG. 5b is a schematic view illustrating a state in which the driving means is provided on the detector constituting the multi-axially variable detection module of a PET apparatus according to the embodiment of the present invention and the detector elements are rotated around the hinges such that the detector is configured in a flat shape.

Since the second drive unit 330 pushes or pulls out the outermost sides of the detector elements 211 as described above, the detector elements 211 are rotated around the hinges such that the detector elements 211 are distributed and arranged in an arc shape as illustrated in FIG. 5b or converged and arranged in a flat shape as illustrated in FIG. 5b.

Figure 5C:
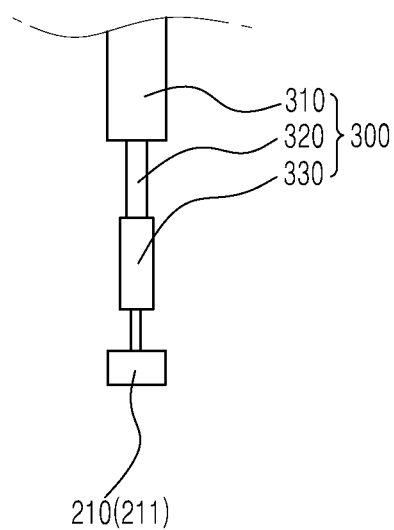
FIG. 5c is a schematic view illustrating a state in which the driving means is provided on the detector constituting the multi-axially variable detection module of a PET apparatus according to the embodiment of the present invention and a detector element of the detector is rotated about a drive shaft.

As illustrated in FIG. 5c, the drive shaft 320 rotates the detector 210 by the rotational power of the first drive unit 310.

Hereinafter, an operation of the multi-axially variable detection module of a PET apparatus according to the embodiment will be described with reference to FIGS. 6 to 8.

Figure 6:
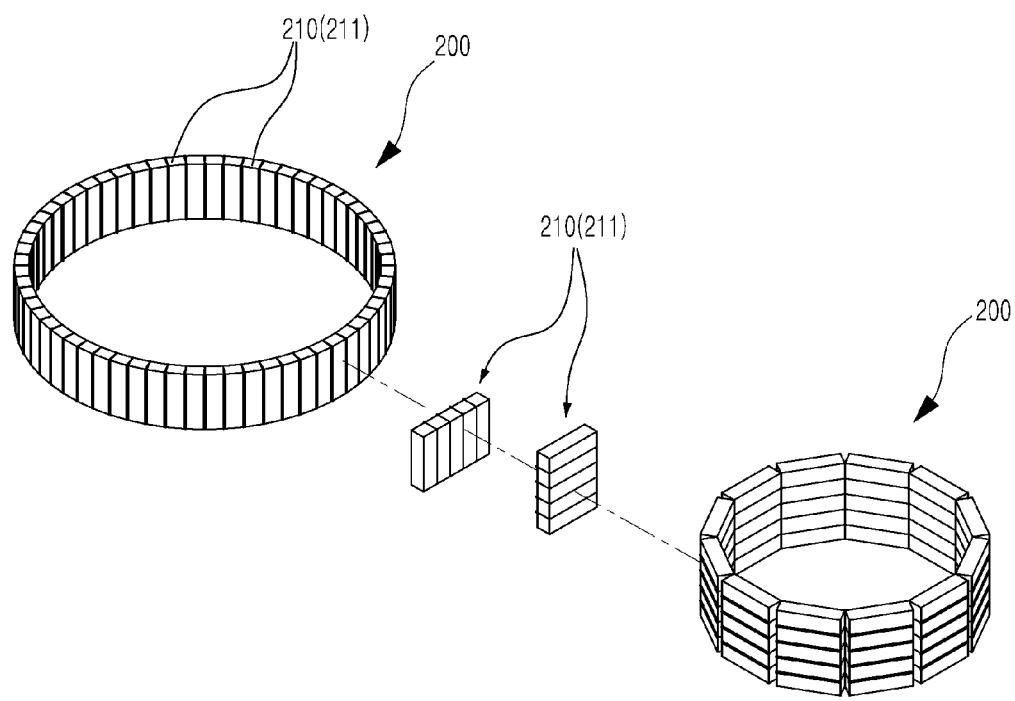
FIG. 6 is a perspective view illustrating a state in which the multi-axially variable detection module of a PET apparatus according to the embodiment of the present invention is variable in length in longitudinal direction of the detection module through the rotation of each detector.

FIG. 6 is a perspective view conceptually illustrating a process in which the variable detection module 200 varies in diameter in the radial direction (the transverse direction).

As illustrated in the figure, in order to reduce the diameter of the detection module 200 from an initial state where the detection module 200 has the maximum diameter for a case where a diameter of a subject is small, the detector elements 211 are rotated so that the detector 210 is converged and arranged in a flat shape. Then, the longitudinal length of the detection module 200 is extended through the rotation of each detector 210.

This is because each detector 210 has a rectangular cross section, and the long sides of the detectors 210 define the inner circumferential curve of the detection module 200 and then become defining the longitudinal length of the detection module 200 through the rotation of the detectors 210.

Thereafter, by driving the detectors 210 linearly in the transverse direction (radial direction) of the detection module 200 in accordance with a diameter of a subject, the diameter of the detection module in the transverse direction is varied and the length in the longitudinal direction is extended whereby a space of emitted radiation for the subject can be secured to a greater extent in the longitudinal direction of the detection module 200.

Here, in order to restore the detection module 200 to the initial state, that is, to provide an environment for imaging a large sized subject, the above-described process is performed reversely.

At this point, the multiple detector elements 211 are rotated about the hinges while the long sides of the detectors 210 define the inner circumferential curve of the detection module 200 such that an arc shape is maintained. Thus, it is possible to maintain the ring shape even when the long sides of the detectors 210 define the inner circumference of the detection module 200, whereby loss in radiation detection can be suppressed as much as possible.

Sequential steps of the process will be described in detail with reference to FIGS. 7 and 8.

Figure 7A:
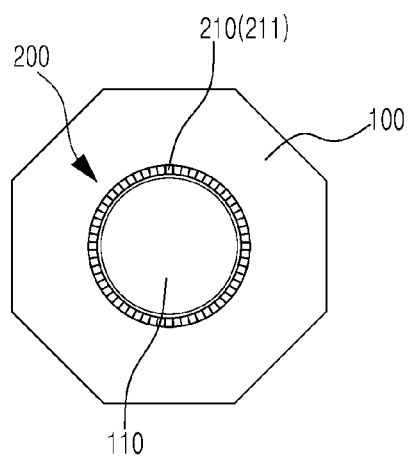
FIGS. 7a to 7e are front views illustrating a process of varying a diameter of the multi-axially variable detection module of a PET apparatus according to the embodiment of the present invention in the radial direction.

FIGS. 7a and 8a illustrate an initial state in which the detection module 200 is positioned on the gantry 100 and the detection module 200 has the maximum diameter.

This state is an environment for imaging a whole body of a human body, and the detector elements 211 are rotated to maintain the shape of the detection module 200 in a substantially ideal circular (annular) shape.

Here, the detectors 210 are provided in a rectangular form having a longer transverse length L1 than a longitudinal length L2 thereof.

Figure 7B:
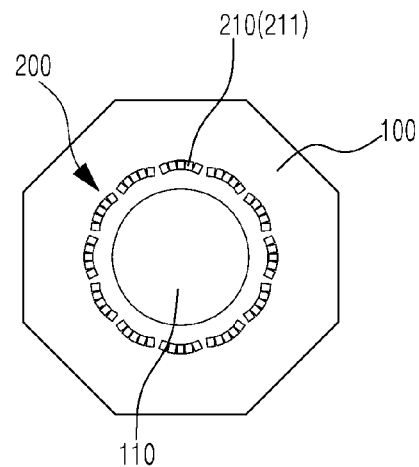

Thereafter, the first drive unit 310 of the driving means 300 is operated to move each detector 210 outwardly of the through-hole 110 as illustrated in FIGS. 7b and 8b.

This is to secure a predetermined distance for rotation of each detector 210.

That is, in order to avoid interference with neighboring detectors 210 when rotating the detectors 210, the detectors 210 are moved outward in the radial direction of the detection module 200 as illustrated in FIG. 7b.

Thereafter, the second drive unit 330 is operated to pull the outermost detector elements 211 such that the detector elements 211 distributed in an arc shape are rotated whereby the detector 210 is arranged in a flat shape.

Figure 7C:
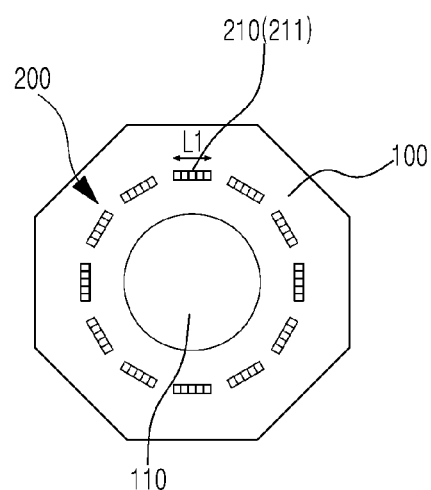

As a result, the detector 210 is configured in a flat shape rather than an arc shape, as illustrated in FIGS. 7c and 8c.

Thereafter, the drive shaft 320 is rotated through the first drive unit 310.

Figure 7D:
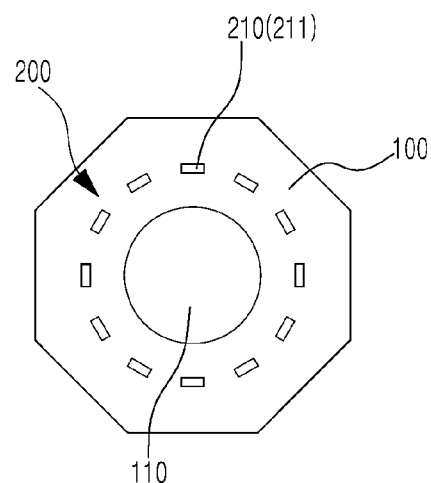

Thus, each detector 210 is rotated in place about the first drive unit 310. The longitudinal length L2 of the detector 210 is shortened to be the transverse length of the detector 210 as illustrated in FIG. 7d and the transverse length L1 of the detector 210 is lengthened to be the longitudinal length as illustrated in FIG. 8d.

Then, the first drive unit 310 is linearly driven to move the detectors 210 whose longitudinal lengths are varied toward the through-hole 110.

Figure 7E:
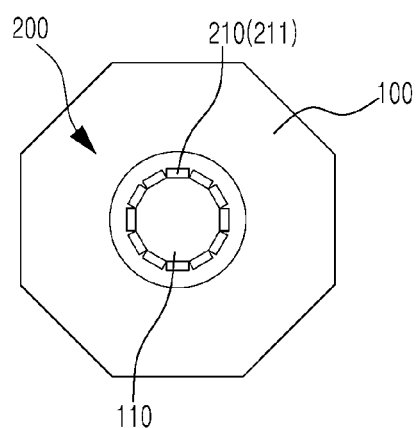

Accordingly, the detectors 210 are moved toward the through-hole 110 as illustrated in FIGS. 7e and 8e, and the detection module 200 is reduced in diameter to fit a size of the subject.

On the other hand, the transverse length L1 and the longitudinal length L2 of each detector 210 may be the same.

In the embodiment, the sectional shape of the detector 210 is exemplified as a rectangle, but the sectional shape of the detector 210 may be provided as a square.

In this case, two or more detectors 210 may be combined to extend the longitudinal length of the detection module 200.

That is, since the length of the detector 210 in the transverse direction is the same as the length of the detector 210 in the longitudinal direction, when the detectors 210 are combined with the adjacent detectors 210 in the transverse direction, the length of the detectors 210 in the transverse direction can be increased.

This configuration is provided as another embodiment of the present invention and will be briefly described with reference to FIG. 9 attached hereto.

Prior to the description, the same reference numerals will be used throughout the drawings and the description to refer to the same or like elements or parts of the embodiment, and a detailed description thereof will be omitted.

Figure 9:
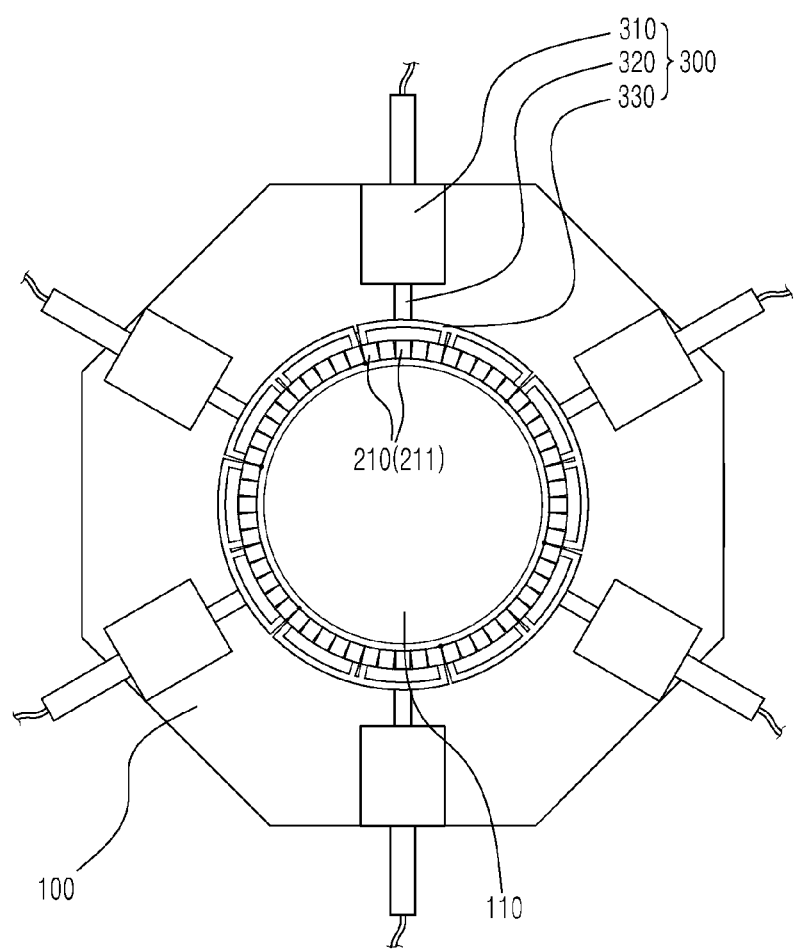
FIG. 9 is a front view illustrating a state in which a multi-axially variable detection module of a PET apparatus according to another embodiment of the present invention is provided on a gantry.

As illustrated in FIG. 9, an annular detection module 200 is provided, and each detector 210 constituting the detection module 200 is combined with neighboring detectors 210 in a hinged manner to form a pair.

Here, the number of the detectors 210 to be combined may be two or more. In this description, a configuration in which two detectors 210 are combined in a hinged manner will be described for convenient description.

Each detector 210 is configured with multiple detector elements 211 as in the embodiment, and the detector elements 211 are engaged to each other in the circumferential direction of the detection module 200 in a hinged manner.

It is obvious that the detector elements 211 are distributed about hinges to form an ideal circular (annular) shape and arranged in an arc shape.

In this state, in order to perform a variable operation for reducing the diameter of the detection module 200, the first drive unit 310 is operated to move a pair of detectors 210 outwardly of a through-hole to secure a space for variable operation.

Then, the second drive unit 330 is operated to converge and arrange the distributed detector elements 211 in a flat shape from the arc shape.

In addition, the second drive unit 330 rotates and arranges a pair of detectors 210 that are kept open at a predetermined angle in a flat shape.

Accordingly, even in the case of the detectors 210 having a square section, a transverse length of the detectors 210 becomes longer than a longitudinal length of the detectors 210.

Thereafter, when rotating a pair of detectors 210 by rotating a drive shaft 320, the longitudinal length of the detection module 200 is extended.

Then, the diameter of the detection module 200 is reduced to provide an environment for imaging a subject such as a brain or a small animal by driving the drive shaft 320 linearly and moving the rotated detectors 210 toward the through-hole 110.

As illustrated in FIGS. 6 and 7, short sides of the detectors 210 define a curve in the longitudinal direction (circumferential direction) of the detection module 200 in a state in which the detection module 200 is reduced in diameter in the transverse direction and is varied in longitudinal length.

Here, since the short sides of the detectors 210 are flat, the shape of the detection module is distant from the ideal annular shape such that the structural sensitivity on the transverse sectional plane may be deteriorated.

In order to prevent the structural sensitivity of the detection module 200 from being deteriorated in a state where the diameter of the detection module 200 is reduced in the transverse direction and is variable in diameter in the longitudinal direction, the detector 210 can be configured in a grid arrangement formed not only in the transverse direction but also in the longitudinal direction.

This configuration is provided as still another embodiment of the present invention, and will be described with reference to FIG. 10 attached hereto.

Prior to the description, the same reference numerals will be used throughout the drawings and the description to refer to the same or like elements or parts of the embodiment, and a detailed description thereof will be omitted.

Figure 10:
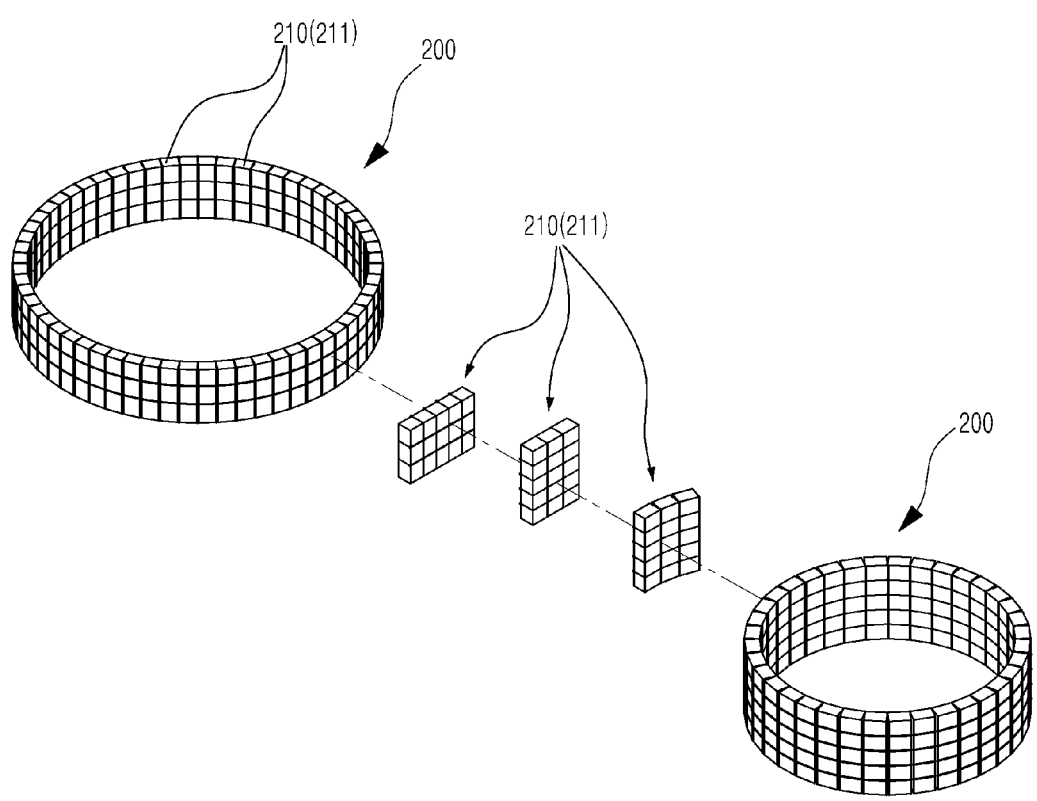
FIG. 10 is a perspective view illustrating a state in which a multi-axially variable detection module of a PET apparatus according to still another embodiment of the present invention is variable in length in longitudinal direction of a detection module through the rotation of each detector.

As illustrated in FIG. 10, a plurality of detectors 210 constituting a detection module 200 is provided, and each of the detectors 210 is configured with detector elements 211 that are configured in a grid arrangement formed in the transverse and longitudinal directions of the detection module 200.

The multiple detector elements 211 are engaged with each other in a hinged manner such that the detectors 210 can be curved about hinges in transverse and longitudinal directions of the detection module 200.

Referring to FIG. 10, a process of varying the detection module 200 according to the embodiment in the transverse and longitudinal directions will be described as follows.

For the configuration of the annular detection module 200, the detector elements 210 arranged to be curved in transverse and longitudinal directions of the detection module 200 are rotated about the hinges and arranged in a flat shape and then vary in length in the longitudinal direction of the detection module 200 through rotation.

Thereafter, the rotated detector 210 arranged in the flat shape is arranged to be curved in an arc shape as illustrated in FIG. 10 through the rotation of the detector elements 211 engaged with each other in the longitudinal direction in a hinged manner.

Then, by moving the detectors 210 toward a through-hole 110, the diameter of the detection module 200 is reduced while the annular shape thereof is maintained. Therefore, even when the detection module 200 is varied multi-axially, it is possible to prevent the structural sensitivity from being deteriorated.

As described above, in the multi-axially variable detection module of a PET apparatus according to the present invention, the size of the detection module in the variable process in which the diameter is reduced according to a size of a subject can be varied not only in the transverse direction but also in the longitudinal direction.

Accordingly, even when a size of a subject is small, it is possible to provide an optimum environment for imaging the subject without providing additional equipment and to maximize the detection efficiency due to ensuring of space for the detection module in the longitudinal direction.

In particular, since the detectors are provided such that the multiple detector elements are engaged with each other in a hinged manner, when the length of the detection module in the longitudinal direction is extended through rotation of each detector constituting the detection module, the detector can be arranged in a flat or an arc shape.

Accordingly, for extending the length of the detector module, even when a length of one side of the detector is long to extend the length of the detection module, the shape of the detection module can be maintained in the ideal annular shape whereby the radiation loss during radiation detection can be suppressed as much as possible.

Although the embodiment of the present invention has been described for illustrative purposes, those skilled in the art will appreciate that various modifications, additions and substitutions are possible, without departing from the scope and spirit of the invention as disclosed in the accompanying claims.

DESCRIPTION OF REFERENCE NUMERALS
IN THE DRAWINGS

100: gantry 110: through-hole
200: detection module 210: detector
211: detector element 300: driving means
310: first drive unit 320: drive shaft
330: second drive unit

What is claimed is:

1. A multi-axially variable detection module of a positron emission tomography (PET) apparatus, the detection module comprising:
   a gantry having a through-hole extending from a side to an opposite side of the gantry;
   a detection module in which a plurality of detectors for detecting gamma rays emitted from a subject are arranged annularly along an inner circumference of the gantry; and
   a driving means for moving the plurality of detectors constituting the detection module in a radial direction of the detection module,
   wherein:
   each of the plurality of detectors is rotatable to vary a length thereof in a longitudinal direction,
   each of the plurality of detectors includes multiple detector elements which are engaged with each other in a hinged manner to form a flat or an arc shape,
   the plurality of detectors include a first detector and a second detector next to the first detector, the first detector has first multiple detector elements and the second detector has second multiple detector elements,
   the first multiple detector elements are movable between a first position to a second position, such that:
   in the first position, the first multiple detector elements are arranged with each other to collectively form a length in the longitudinal direction and a length in a transverse direction of the first detector which are different from each other, and
   the first multiple detector elements are rotatable together while being engaged with each other in the hinged manner to the second position, such that a length in the transverse direction of the first detector in the second position is defined by the length in the longitudinal direction of the first detector in the first position, and a length in the longitudinal direction of the first detector in the second position is defined by the length in the transverse direction of the first detector in the first position.

2. The detection module of claim 1, wherein two or more detectors are engaged with each other in a hinged manner to constitute the detector module.

3. The detection module of claim 2, wherein the driving means is configured to generate power for rotating the detector, and to push or pull end sides of the multiple detector elements to arrange the detectors to form the flat or the arc shape.

4. The detection module of claim 2, wherein the multiple detector elements are configured in a grid arrangement in the longitudinal and transverse directions of the detection module, and
the detector elements configured in the grid arrangement are engaged with each other in a hinged manner in the longitudinal direction and the transverse direction.

5. The detection module of claim 1, wherein the driving means is configured to generate power for rotating the detector, and to push or pull end sides of the multiple detector elements to arrange the detectors to form the flat or the arc shape.

6. The detection module of claim 5, wherein the driving means includes:
   a first drive unit generating linear driving force and rotational power;
   a drive shaft linearly moved by the power of the first drive unit and rotated about the first drive unit; and
   a second drive unit branched from the drive shaft into two ends, corresponding to the outermost detector elements constituting the detector, and generating a translational force.

7. The detection module of claim 6, wherein the driving means includes:
   a first drive unit generating linear driving force and rotational power;
   a drive shaft linearly moved by the power of the first drive unit and rotated about the first drive unit; and
   a second drive unit branched from the drive shaft into two ends, corresponding to the outermost detector elements constituting the detector, and generating a translational force.

8. The detection module of claim 1, wherein the multiple detector elements are configured in a grid arrangement in the longitudinal and transverse directions of the detection module, and
the detector elements configured in the grid arrangement are engaged with each other in a hinged manner in the longitudinal direction and the transverse direction.

9. The detection module of claim 8, wherein
in the first position, the first multiple detector elements in the grid arrangement form a first arc shape in the longitudinal direction, move away from the through-hole, rotate about hinges to be in the flat shape in the longitudinal direction, turn 90 degrees, rotate about hinges to form a second arc shape, and move toward the through-hole to be in the second position with the first multiple detector elements forming the flat shape in the transverse direction of the first detector in the second position and forming the second arc shape in the longitudinal direction of the first detector in the second position.

10. The detection module of claim 1, wherein:
   a number of the second multiple detector elements is same as a number of the first multiple detector elements,
   the second multiple detector elements are movable between a first position to a second position, such that:
   in the first position, the second multiple detector elements are arranged with each other to collectively form a length in the longitudinal direction and a length in a transverse direction of the second detector, and
   the second multiple detector elements are rotatable together while being engaged with each other in the hinged manner to the second position, such that a length in the transverse direction of the second detector in the second position is defined by the length in the longitudinal direction of the second detector in the first position, and a length in the longitudinal direction of the second detector in the second position is defined by the length in the transverse direction of the second detector in the first position.

11. The detection module of claim 1, wherein:
in the first position, the first multiple detector elements form the arc shape in the longitudinal direction, move away from the through-hole, rotate about hinges to be in the flat shape in the longitudinal direction, turn 90 degrees and move toward the through-hole to be in the second position with the flat shape being formed in the transverse direction of the first detector in the second position.

* * * * *